United States Patent [19]

Rhee et al.

[11] Patent Number: 5,614,587
[45] Date of Patent: Mar. 25, 1997

[54] COLLAGEN-BASED BIOADHESIVE COMPOSITIONS

[75] Inventors: Woonza M. Rhee, Palo Alto; Prema R. Rao, Los Gatos; George H. Chu, Cupertino; Frank A. DeLustro, Belmont; Carol F. H. Harner, Redwood Shores; Naomi Sakai, San Mateo; Jacqueline A. Schroeder, Redwood City, all of Calif.

[73] Assignee: Collagen Corporation, Palo Alto, Calif.

[21] Appl. No.: 476,825

[22] Filed: Jun. 7, 1995

Related U.S. Application Data

[63] Continuation-in-part of Ser. No. 147,227, Nov. 3, 1993, which is a continuation-in-part of Ser. No. 922,541, Jul. 30, 1992, Pat. No. 5,328,955, which is a continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^6$ .......................... A61F 13/00; A61B 17/04
[52] U.S. Cl. ........................ 525/54.1; 602/52; 602/54; 606/229
[58] Field of Search ................ 525/54.1; 602/52, 602/54; 606/229

[56] References Cited

U.S. PATENT DOCUMENTS

| | | | |
|---|---|---|---|
| 5,024,742 | 6/1991 | Nesburn et al. | |
| 5,156,613 | 10/1992 | Sawyer | 606/213 |
| 5,162,430 | 11/1992 | Rhee et al. | 525/54.1 |
| 5,192,316 | 3/1993 | Ting | 623/5 |
| 5,209,776 | 5/1993 | Bass et al. | 106/124 |
| 5,219,895 | 6/1993 | Kelman et al. | 522/68 |
| 5,290,552 | 3/1994 | Sierra et al. | 424/94.64 |
| 5,328,955 | 7/1994 | Rhee et al. | 525/54.1 |
| 5,475,052 | 12/1995 | Rhee et al. | 525/54.1 |

FOREIGN PATENT DOCUMENTS

| | | |
|---|---|---|
| 341007 | 11/1989 | European Pat. Off. |
| 466383 | 1/1992 | European Pat. Off. |
| 575273 | 12/1993 | European Pat. Off. |
| 60-70972 | 3/1994 | Japan |
| WO92/13578 | 8/1992 | WIPO |

*Primary Examiner*—Nathan M. Nutter
*Attorney, Agent, or Firm*—Kathi Rafayko

[57] ABSTRACT

Collagen-based compositions useful in the attachment of tissues, or the attachment of tissues to synthetic implant materials, are disclosed. The compositions comprise collagen crosslinked using a multifunctionally activated synthetic hydrophilic polymer. A particularly preferred composition comprises fibrillar collagen, a fiber disassembly agent, and a multifunctionally activated synthetic hydrophilic polymer. Methods are disclosed for using the compositions to effect the attachment of a native tissue to the surface of another native tissue, a non-native tissue, or a synthetic implant.

8 Claims, 3 Drawing Sheets

COLLAGEN-BASED BIOADHESIVE COMPOSITIONS

CROSS REFERENCES

This application is a continuation-in-part of allowed U.S. application Ser. No. 08/147,227, filed Nov. 3, 1993, which is a continuation-in-part of Ser. No. 922,541, filed Jul. 30, 1992, now U.S. Pat. No. 5,328,955, issued Jul. 12, 1994, which is a continuation-in-part of Ser. No. 433,741, filed Nov. 14, 1989, now U.S. Pat. No. 5,162,430, issued Nov. 10, 1992, which is a continuation-in-part of U.S. application Ser. No. 07/274,071, filed Nov. 21, 1988, subsequently abandoned, which applications and issued patents are incorporated herein by reference in full, and to which currently pending application we claim priority under 35 U.S.C. §120.

FIELD OF THE INVENTION

This invention relates generally to compositions useful as biological or surgical adhesives; more specifically, it relates to bioadhesive compositions comprising collagen crosslinked using a multifunctionally activated synthetic hydrophilic polymer, as well as methods of using such compositions to effect adhesion between a first surface and a second surface, wherein at least one of the first and second surfaces is preferably a native tissue surface.

BACKGROUND OF THE INVENTION

U.S. Pat. No. 5,024,742, issued Jun. 18, 1991, to Nesburn et al., discloses a method of crosslinking amino acid-containing polymers with photoactivatable, heterobifunctional crosslinking agents, the crosslinking agents having a photoactivatable site and a conventional site, comprising: i) selecting one or more amino acid-containing polymers; and ii) combining the polymers with the crosslinking agents such that the conventional site on the crosslinking agent is bound to the polymer and the photoactivatable site is unbound. Upon photoactivation, crosslinks are formed when the photoactive site binds to another amino acid-containing polymer. The resulting crosslinked collagen composition can be used as a bioadhesive for sutureles closures of the eye or any other wound.

U.S. Pat. No. 5,156,613, issued Oct. 20, 1992, to Sawyer, discloses a method of joining or reconstructing biological tissue comprising applying energy to the tissue while providing a filler material to is and denaturing or melting the material and adjacent biological tissue with the energy to cause mixing of the denatured or melted filler material and tissue, thus joining or reconstructing the tissue. Also claimed is a method of joining or reconstructing biological tissue comprising applying optical or radio frequency energy while providing a collagen filler material to the biological tissue; denaturing or melting the collagen and adjacent tissue with the applied energy to cause mixing of the denatured or melted collagen and tissue; and joining or reconstructing the tissue.

U.S. Pat. No. 5,162,430, issued Nov. 10, 1992, to Rhee et al., and commonly owned by the assignee of the present invention, discloses collagen - synthetic polymer conjugates prepared by covalently binding collagen to synthetic hydrophilic polymers such as various derivatives of polyethylene glycol.

U.S. Pat. No. 5,192,316, issued Mar. 9, 1993, to Ting, discloses a lens for implantation directly on the Bowman's membrane of a live cornea to correct the optical properties of the eye. The lens is made of a synthetic polymer which is permeable to water and forms a hydrogel. The lens preferably includes an additive to increase the adhesion of the lens to the cornea and/or to stimulate the growth of epithelial cells. The additive may be fibronectin, collagen, cell fastening protein, antigelatin factor, a biologically active peptide, cold insoluble globulin, chondronectin, lanlinin, epithelial growth factor (EGF), or a mixture thereof.

U.S. Pat. No. 5,209,776, issued May 11, 1993, to Bass et al., discloses a composition for bonding separated tissues together or for coating tissues or prosthetic materials comprising: i) at least one first component selected from natural or synthetic peptides, modified, crosslinked, cleaved, or shortened variants or derivatives, and ii) at least one second component, which is different from the first component, adapted to support the first component to form a matrix, sol, or gel with the first component. The first component may be, for example, albumin, alpha-globulins, beta-globulins, gamma-globulins, transthyretin, fibrinogen, thrombin, collagen, elastin, keratin, fibroin, fibrin, or fibronectin. The second component may be, for example, hyaluronic acid, chondroitin sulfate, dennatan sulfate, keratan sulfate, heparin, heparan sulfate, collagen, fructose, dextrans, agarose, alginic acid, pectins, methylcellulose, hydroxycellulose, hydroxypropylmethylcelulose, hydroxyethylecellulose, CMC, glycerin, mannitol, sorbitol, polyvinylalcohol, or polyethylene glycol.

U.S. Pat. No. 5,219,895, issued Jun. 15, 1993, to DeVore et al., discloses a collagen composition, useful as an adhesive for medical applications, wherein the composition is formed by the polymerization of derivatized collagen, modified with an acylating agent and/or a sulfonating agent. The polymerization is performed by explosive UV irradiation, fluorescent light, and/or an initiator. The acylating agent may be glutaric arthydride, succinic anhydride, lauric anhydride, diglycolic anhydride, methyl succinic arthydride, methyl glutaric arthydride, dimethyl glutaric anhydride, or exo-3,6epoxy-1,2,3,4-tetrahydrophthalic arthydride. Bonding of soft tissue comprises applying a polymerizable collagen composition onto at least a portion of a surface of at least one of a first and second tissue; exposing the tissue surface to an initiator to polymerize the collagen; and contacting the two tissues to form a bond between them.

U.S. Pat. No. 5,290,552, issued Mar. 1, 1994, to Brown et al., discloses a surgical adhesive composition comprising fibrinogen, actor XIII, collagen, thrombin, and $Ca^{2+}$ ions in an aqueous medium. The collagen is fibrillar, is insoluble at pH values about 5, is flowable, has the native helical structure of collagen fibrils, and is capable of causing gelation of the adhesive. The thrombin and $Ca^{2+}$ are present in an amount sufficient to catalyze polymerization of the fibrinogen to form a clot.

Commonly owned U.S. Pat. No. 5,328,955, issued Jul. 12, 1994, to Rhee et al., discloses various activated forms of polyethylene glycol and various linkages which can be used to produce collagen—synthetic polymer conjugates having a range of physical and chemical properties.

European patent publication No. 341007, to Matrix Pharmaceuticals, Inc., discloses a surgical adhesive composition comprising, in an aqueous composition, plasma from the patient to be treated, collagen in an amount sufficient to thicken the composition (e.g., at a concentration of about 5–30 mg/ml), and thrombin in an amount sufficient to catalyze polymerization of fibrinogen present in the plasma to produce a clot (e.g., about 1–1000 N1Hu thrombin).

European patent publication No. 466383, to Bausch & Lomb Inc., discloses an adhesive composition suitable for surgical applications comprising an aqueous solution of natural collagen which has a melt index temperature of 35°–45° C. The composition comprises a blend of densely crosslinked collagen and non-crosslinked collagen. The densely crosslinked collagen is achieved by thermal crosslinking. PCT publication No. WO 9213578, to Bausch & Lomb Inc., discloses a surgical adhesive composition comprising an aqueous collagen or gelatin solution with a melt index temperature (MIT) of 33°–60° C. Healing of wounds is promoted by contacting at least one surface of the wound with a composition comprising: a) a dispersion of cultured epithelial cells in an aqueous collagen solution, or b) an aqueous solution containing a purified naturally occurring biopolymer and growth factors, wherein the composition has an MIT of 33°–60° C. and a viscosity of less than 50,000 cP at 10° C. above the MIT.

European patent publication No. 575273, to Flamel Technologies, discloses crosslinkable collagen derivatives that are soluble in water and/or polar aprotic organic solvents and contain free or substituted —SH groups on cysteine or cysteine derivative residues attached to the collagen molecule, at least in part, through spacer groups. Also disclosed is insoluble crosslinked collagen in which the interchain bridges are, at least in part, disulfide linkages formed by cysteine residues attached to the collagen molecule, at least in part, through spacer groups. The claimed compositions are useful as biological or surgical adhesives.

Japanese patent publication No. 6070972, to Nippon, discloses a composition for adhering biological tissues consisting of i) an adhesive ingredient comprising a partial hydrolysate of collagen protein, water, and a polyhydric phenol compound; and ii) a hardening ingredient consisting of an aqueous solution containing at least one of formaldehyde, glutaraldehyde, and glycerol aldehyde.

Commonly owned, allowed U.S. application Ser. No. 08/147,227, filed Nov. 3, 1993, by Rhee et al., discloses collagen-polymer conjugates comprising chemically modified collagens, which are in substantially nonfibrillar form at pH 7, covalently bound to synthetic hydrophilic polymers to produce optically clear materials for use in ophthalmic or other medical applications.

Each publication cited above and herein is incorporated herein by reference in its entirety to describe and disclose the subject matter for which it is cited.

We now disclose a detailed description of preferred embodiments of the present invention, including bioadhesive compositions comprising collagen crosslinked using multifunctionally activated synthetic hydrophilic polymers, and methods for using these compositions to effect adhesion between a first surface and a second surface, wherein at least one of the first and second surfaces is a native tissue surface.

SUMMARY OF THE INVENTION

The present invention discloses compositions suitable for use as bioadhesives, which compositions comprise fibrillar collagen, a fiber disassembly agent, and a multifunctionally activated synthetic hydrophilic polymer, wherein the fiber disassembly agent is present in an amount sufficient to render the collagen substantially nonfibrillar at pH 7, and the collagen and synthetic polymer covalently bind to form a collagen—synthetic polymer conjugate. A particularly preferred composition of the invention comprises fibrillar collagen, a biocompatible alcohol, and a multifunctionally activated synthetic hydrophilic polymer, wherein the biocompatible alcohol is present in an amount sufficient to render the collagen substantially nonfibrillar at pH 7, and the collagen and synthetic polymer covalently bind to form a collagen—synthetic polymer conjugate.

In a general method for effecting the attachment of a first surface to a second surface, collagen and a multifunctionally activated synthetic hydrophilic polymer are mixed to initiate crosslinking, the collagen—synthetic polymer mixture is applied to a first surface before substantial crosslinking has occurred between the collagen and the synthetic polymer, then a second surface is brought into contact with the first surface. At least one of the first and second surfaces is preferably a native tissue surface.

In a particularly preferred method for effecting the attachment of a first surface to a second surface, nonfibrillar collagen and a multifunctionally activated synthetic hydrophilic polymer are mixed to initiate crosslinking, the nonfibrillar collagen—synthetic polymer mixture is applied to a first surface before substantial crosslinking has occurred between the collagen and the synthetic polymer, then a second surface is brought into contact with the first surface. At least one of the first and second surfaces is preferably a native tissue surface.

The nonfibrillar collagen-based adhesive compositions of the present invention are optically clear, making the compositions and methods of the present invention particularly suited for use in ophthalmic applications in which optical clarity is a requirement. Furthermore, the compositions of the present invention are comprised of biocompatible, nonimmunogenic components which leave no toxic, potentially inflammatory or immunogenic reaction products at the tissue site of administration.

DETAILED DESCRIPTION OF THE PREFERRED EMBODIMENTS OF THE INVENTION

Figure 1:
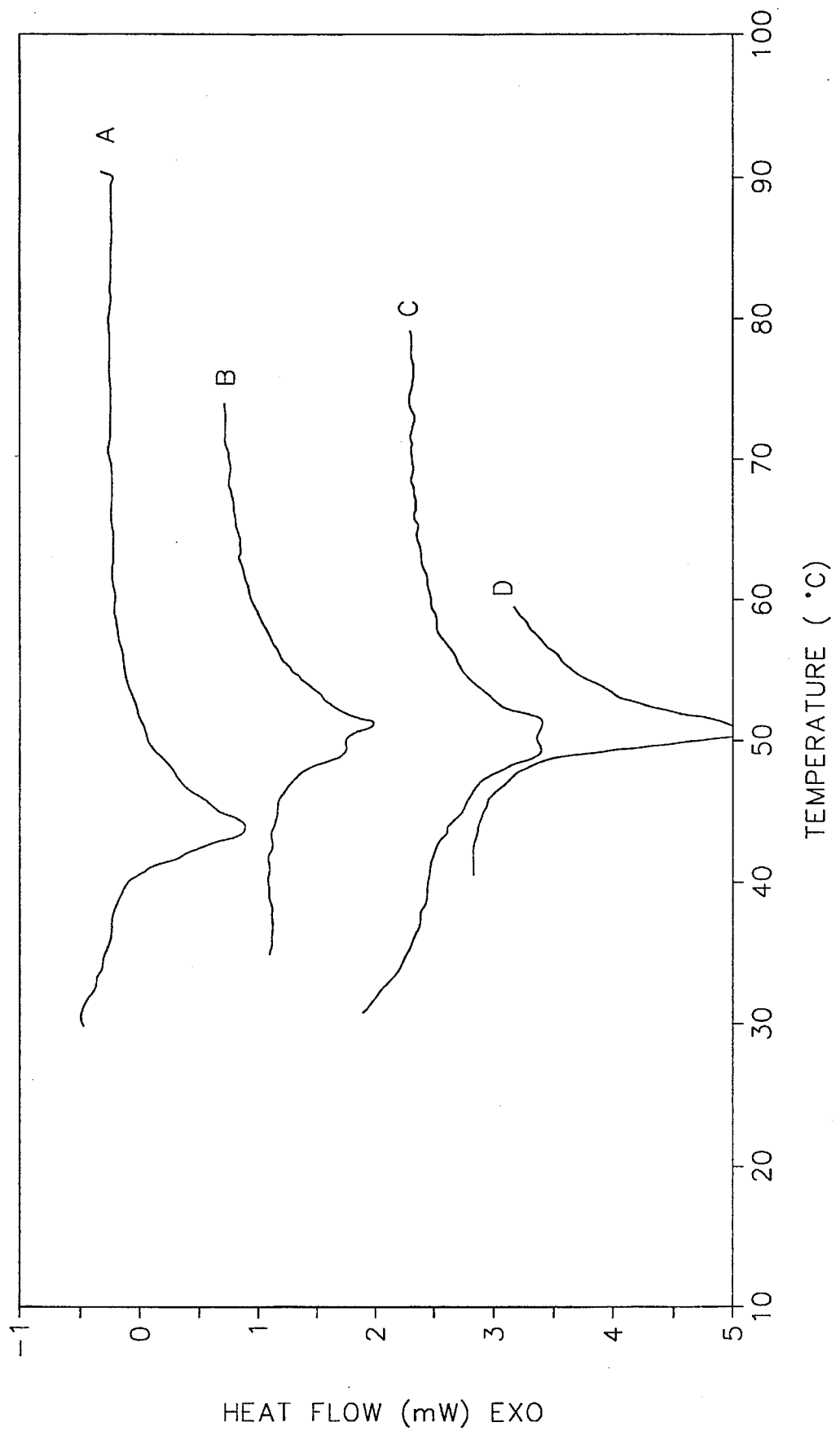
FIG. 1 shows differential scanning calorimetry (DSC) results for noncrosslinked succinylated collagen (Sample A) and succinylated collagen formulations containing 10, 20, 50, and 91 mg/ml difunctionally activated SG-PEG (Samples B, C, and D, respectively).

In accordance with the present invention, compositions suitable for use as biological or surgical adhesives are prepared by crosslinking collagen with a multifunctionally activated synthetic hydrophilic polymer. As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and a non-native tissue surface or a surface of a synthetic implant.

In order to prepare the bioadhesive compositions of the present invention, it is first necessary to provide collagen and a multifunctionally activated synthetic hydrophilic polymer.

Collagen is the major protein component of bone, cartilage, skin, and connective tissue in animals. Collagen in its native form is typically a rigid, rod-shaped molecule approximately 300 nanometers (nm) long and 1.5 nm in diameter. It is comprised of three collagen polypeptides which form a tight triple helix. The collagen polypeptides are characterized by a long midsection having the repeating sequence —Gly—X—Y—, where X and Y are often proline or hydroxyproline, bounded at each end by the "telopeptide" regions, which constitute less than about 5 percent (%) of the molecule. The telopeptide region of the collagen chains are typically responsible for the crosslinking between chains and for the immunogenicity of the protein.

In general, collagen from any source may be used to prepare the compositions of the present invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is basically a three-step process involving solubilization, enzyme treatment, and purification, as described in U.S. Pat. No. 4,140,537, issued Feb. 20, 1979, to Luck et al., and U.S. Pat. No. 4,488,911, issued Dec.18, 1984, to Luck et al., which are incorporated herein by reference. Commonly owned, allowed U.S. patent application Ser. No. 07/921,810, filed Jul. 29, 1992, discloses methods of extracting and purifying collagen from the human placenta. Commonly owned, copending U.S. application Ser. No. 08/183,648, filed Jan. 18, 1992, discloses methods of producing recombinant human collagen in the milk of transgenic animals, including transgenic cows. The term "collagen" or "collagen material" as used herein refers to all forms of collagen, including those which have been processed or otherwise modified.

Collagen of any type, including, but not limited to, types I, II, III, IV, or any combination thereof, may be used, although type I is generally preferred. Either alelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use as a starting material in the practice of the present invention, although previously crosslinked collagen may be used. Non-crosslinked atelopeptide fibrillar collagen is commercially available from Collagen Corporation (Palo Alto, Calif.) at collagen concentrations of 35 mg/ml and 65 mg/ml under the trademarks Zyderm® I Collagen and Zydenn II Collagen, respectively. Glutaraldehyde crosslinked atelopeptide fibrillar collagen is commercially available from Collagen Corporation at a collagen concentration of 35 mg/ml under the trademark Zyplast® Collagen. Collagens for use in the present invention are generally in aqueous suspension at a concentration between about 20 mg/ml to about 120 mg/ml; preferably, between about 30 mg/ml to about 90 mg/ml.

Although intact collagen is preferred, denatured collagen, commonly known as gelatin, can also be used in the methods of the invention.

Nonfibrillar collagen is preferred for use in the practice of the present invention because it has a tacky consistency and is generally more viscous than fibrillar collagen (given equivalent collagen protein concentrations), making it particularly useful in compositions intended for use as bioadhesives. The term "nonfibrillar collagen" refers to any modified or unmodified collagen material that is in substantially nonfibrillar form at pH 7, as indicated by optical clarity of an aqueous suspension of the collagen.

Collagens for use in the bioadhesive compositions of the present invention typically start out in fibrillar form, and then are rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Collagen that is already in nonfibrillar form may also be used to prepare the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or microfibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Our experiments have indicated that, due to its inherent tackiness, methylated collagen is particularly preferred for use in bioadhesive compositions (see Examples 3–5, below).

Fibrillar collagen may also be used in the methods of the invention, although it is generally less preferred because it is opaque and less tacky than nonfibrillar collagen. However, fibrillar collagen, or mixtures of nonfibrillar and fibrillar collagen, may be preferred for use in adhesive compositions intended for long-term persistence in vivo, if optical clarity is not a requirement. We have found that mixtures of methylated (nonfibrillar) collagen and fibrillar collagen crosslinked with synthetic hydrophilic polymers are useful as bioadhesives (see Example 5, below).

A composition comprising a mixture of particulate crosslinked fibrillar collagen and noncrosslinked fibrillar collagen, which is disclosed in commonly owned, copending U.S. application Ser. No. 08/344,040, filed Nov. 23, 1994, by Rhee et al., may also be used in the practice of the invention. The particulate crosslinked fibrillar collagen is preferably glutaraldehyde-crosslinked fibrillar collagen and preferably comprises between about 25 to about 95 percent, more preferably, between about 60 to about 80 percent by weight, of the final composition. The noncrosslinked fibrillar collagen preferably comprises between about 5 to about 75, more preferably, between about 20 to about 40 percent by weight, of the final composition. The particulate crosslinked fibrillar collagen and noncrosslinked fibrillar collagen are first combined, then crosslinked together using a synthetic hydrophilic polymer.

The collagen-based bioadhesive compositions of the present invention may also be formulated to contain biologically active agents in order to facilitate adhesion of tissues or healing of adhered tissues. The tema "biologically active agent" or "active agent" as used herein refers to organic molecules which exert biological effects in vivo. Examples of active agents include, without limitation, enzymes, receptor antagonists or agonists, hormones, growth factors, autogenous bone marrow, antibiotics, antimicrobial agents, and antibodies. The term "active agent" is also intended to encompass various cell types which can be incorporated into the compositions of the invention. The term "active agent" is also intended to encompass combinations or mixtures of two or more active agents, as defined above.

Preferred active agents for use in the present invention include growth factors and, in particular, members of the transforming growth factor (TGF) supergene family, which are multifunctional regulatory proteins. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the collagen by admixture. Alternatively, the agents may be covalently linked to the collagen using a crosslinking agent such as a functionally activated polyethylene glycol, or affinity bound to the collagen using a binding ligand. Processes for covalently binding biologically active agents such as growth factors to collagen using a synthetic hydrophilic polymer, such as a functTnally activated polyethylene glycol, are described in commonly assigned U.S. Pat. No. 5,162,430, issued Nov. 10, 1992, to Rhee et al.. Processes for affinity binding biologically active agents to collagen via binding ligands such as heparin are disclosed in commonly owned, copending U.S. application Ser. No. 08/405,320, filed Mar. 16, 1995, by Schroeder et al.

The biologically active agent is generally incorporated into the collagen after the collagen has been mixed with a fiber disassembly agent. The type and amount of active agent used will depend, among other factors, on the particular site and condition to be treated and the biological activity and pharmacokinetics of the active agent selected.

When biologically active agents are incorporated into the compositions of the invention, biocompatible alcohols (and, in particular, glycerol) are the preferred fiber disassembly agent, because certain growth factors, such as transforming growth factor beta, have been shown to retain their activity in compositions containing glycerol.

To prepare the collagen-based bioadhesive compositions of the present invention, collagen is crosslinked using a multifunctionally activated synthetic hydrophilic polymer. The term "multifunctionally activated" refers to synthetic hydrophilic polymers which have, or have been chemically modified to have, two or more functional groups located at various sites along the polymer chain and are capable of reacting with primary amino groups on collagen molecules. Each functional group on a multifunctionally activated synthetic hydrophilic polymer molecule is capable of covalently binding with a collagen molecule, thereby effecting crosslinking between the collagen molecules. Types of multifunctionally activated hydrophilic synthetic polymers include difunctionally activated, tetrafunctionally activated, and starbranched polymers.

Multifunctionally activated polyethylene glycols and, in particular, certain difunctionally activated polyethylene glycols, are the preferred synthetic hydrophilic polymers for use in preparing the compositions of the present invention. The term "difunctionally activated" refers to synthetic hydrophilic polymer molecules which have, or have been chemically modified to have, two functional groups capable of reacting with primary amino groups on collagen molecules. The two functional groups on a difunctionally activated synthetic hydrophilic polymer are generally located at opposite ends of the polymer chain. Each functionally activated group on a difunctionally activated synthetic hydrophilic polymer molecule is capable of covalently binding with a collagen molecule, thereby effecting crosslinking between the collagen molecules.

For use in the present invention, molecules of polyethylene glycol (PEG) are chemically modified in order to provide functional groups on two or more sites along the length of the PEG molecule, so that covalent binding can occur between the PEG and reactive groups on the collagen. Some specific activated forms of PEG are shown structurally below, as are generalized reaction products obtained by reacting difunctionally activated forms of PEG with collagen. In Formulas 1–8, the term COL represents collagen; the term PEG represents polymers having the repeating structure $(OCH_2CH_2)_n$.

The first activated PEG is difunctionally activated PEG succinimidyl glutarate, referred to herein as (SG-PEG). The structural formula of this molecule and the reaction product obtained by reacting it with collagen are shown in Formula 1.

FORMULA 1
SG-PEG: Difunctionally Activated PEG Succinimidyl Glutarate

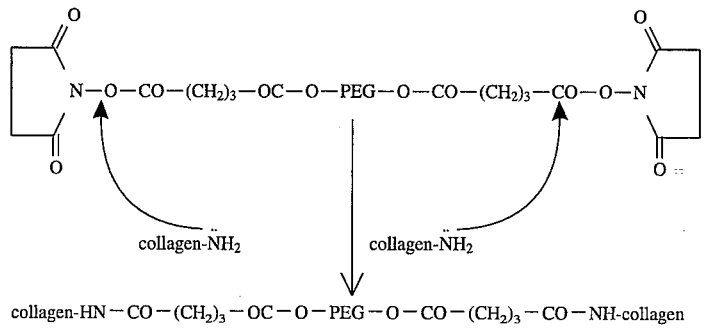

Another difunctionally activated form of PEG is referred to as PEG succinimidyl (S-PEG). The structural formula for this compound and the reaction product obtained by reacting it with collagen is shown in Formula 2. In a general structural formula for the compound, the subscript 3 is replaced with an "n". In the embodiment shown in Formula 1, n=3, in that there are three repeating $CH_2$ groups on either side of the PEG.

The structure in Formula 2 results in a conjugate which includes an "ether" linkage which is less subject to hydrolysis. This is distinct from the conjugate shown in Formula 1, wherein an ester linkage is provided. The ester linkage is subject to hydrolysis under physiological conditions.

FORMULA 2
SE-PEG, n = 3: Difunctionally Activated PEG Succinimidyl (Ether Linkage)

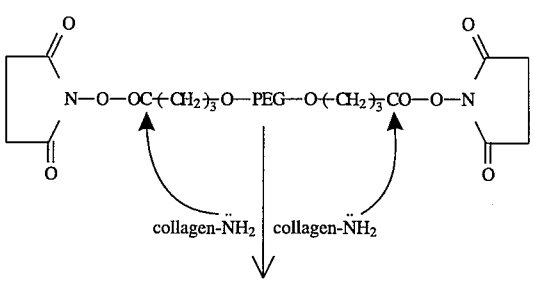

Yet another difunctionally activated form of polyethylene glycol, wherein n=2, is shown in Formula 3, as is the conjugate formed by reacting the activated PEG with collagen.

FORMULA 3
SE-PEG, n = 2: Difunctionally Activated PEG Succinimidyl (Ether Linkage)

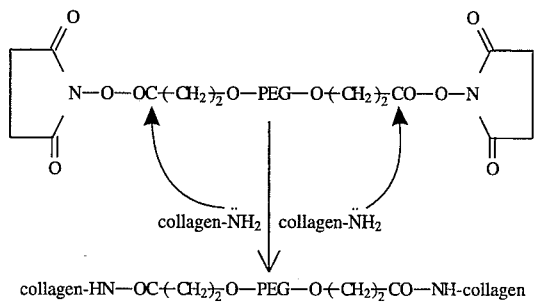

Another preferred embodiment of the invention similar to the compounds of Formulas 2 and 3 is provided when n=1. The structural formula and resulting collagen-synthetic polymer conjugate are shown in Formula 4. It is noted that this conjugate includes both an ether and a peptide linkage. These linkages are stable under physiological conditions.

FORMULA 4
SE-PEG, n = 1: Difunctionally Activated PEG Succinimidyl (Ether Linkage)

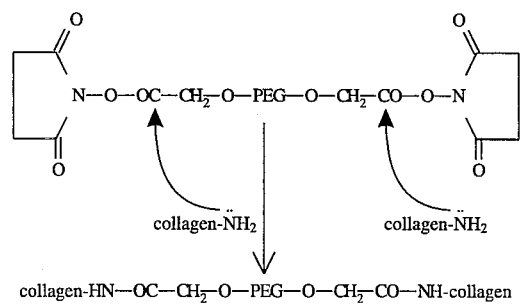

Another difunctionally activated form of PEG is referred to as PEG succinimidyl succinamide (SSA-PEG). The structural formula for this compound and the reaction product obtained by reacting it with collagen is shown in Formula 5. In the structure shown in Formula 1, n=2; however, related compounds, wherein n=1 or n=3–10, may also be used in the practice of the invention.

The structure in Formula 5 results in a conjugate which includes an "amide" linkage which, like the ether linkage previously described, is less subject to hydrolysis and is therefore more stable than an ester linkage.

FORMULA 5
SSA-PEG, n = 2: Difunctionally Activated PEG Succinimidyl Succinamide

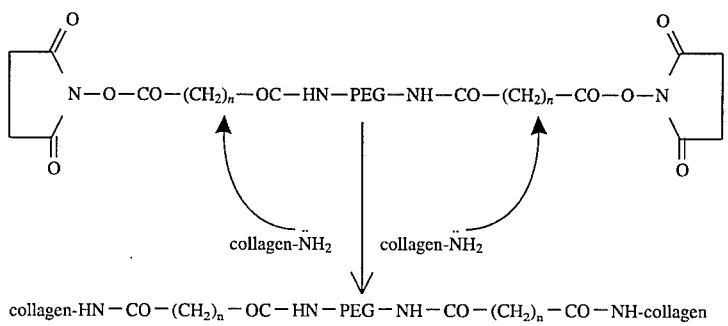

Yet another difunctionally activated form of PEG is provided when n=0. This compound is referred to as PEG succinimidyl carbonate (SC-PEG). The structural formula of this compound and the conjugate formed by reacting SC-PEG with collagen is shown in Formula 6.

FORMULA 6
SC-PEG, n = 0: Difunctionally Activated PEG Succinimidyl Carbonate

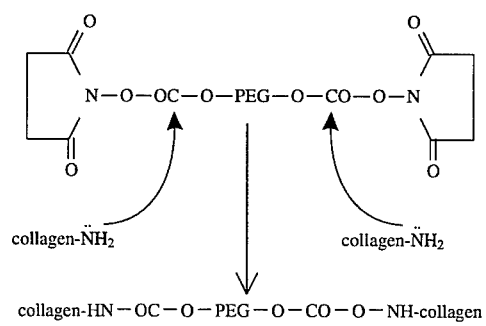

All of the activated polyethylene glycol derivatives depicted in Formulas 1–6 involve the inclusion of the succinimidyl group. However, different activating groups can be attached at sites along the length of the PEG molecule. For example, PEG can be derivatized to form difunctionally activated PEG propion aldehyde (A-PEG), which is shown in Formula 7, as is the conjugate toned by the reaction of A-PEG with collagen. The linkage shown in Formula is referred to as a —$(CH_2)_n$—NH— linkage, where n=1–10.

FORMULA 7
A-PEG: Difunctionally Activated PEG Propion Aldehyde

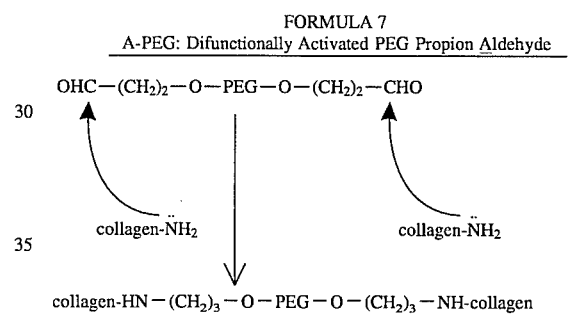

Yet another form of activated polyethylene glycol is difunctionally activated PEG glycidyl ether (E-PEG), which is shown in Formula 8, as is the conjugate formed by reacting such with collagen.

FORMULA 8
E-PEG: Difunctionally Activated PEG Glycidyl Ether

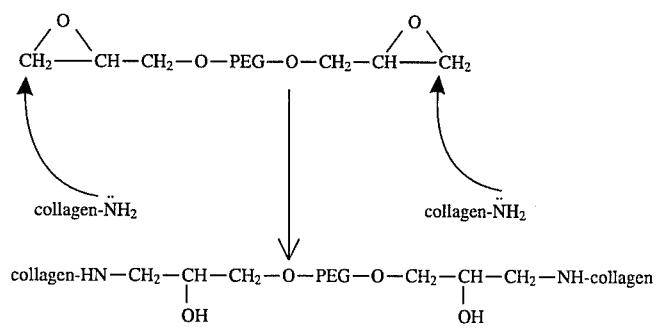

Many of the activated forms of polyethylene glycol described above are now available commercially from Shearwater Polymers, Huntsville, Alabama, and Union Carbide, South Charleston, West Virginia. The various activated forms of polyethylene glycol and various linkages which can be used to produce collagen—synthetic polymer conjugates having a range of physical and 9heroical properties are described in further detail in commonly owned U.S. Pat. No. 5,328,955, issued Jul. 12, 1994, to Rhee et al..

The concentration of multifunctionally activated synthetic hydrophilic polymer used to prepare the compositions of the present invention will vary depending upon a number of factors, including the type and molecular weight of the synthetic polymer used and the collagen protein concentration of the collagen suspension. In general, we have found that synthetic polymer concentrations in the range of about 0.1 to about 10 percent by weight of the final composition are preferred for use in the compositions and methods of the present invention. For example, a final composition having a total weight of 1 gram (1000 milligrams) would contain between about 1 to about 100 milligrams of multifunctionally activated synthetic polymer.

Preferred multifunctionally activated polyethylene glycols for use in the present invention are difunctionally activated SG-PEG (as depicted in Formula 1) and difunctionally activated SE-PEG (shown in Formulas 2–4).

In a general method for preparing the preferred bioadhesive compositions of the invention, an aqueous suspension of fibrillar collagen is mixed with a fiber disassembly agent in an amount sufficient to render the collagen substantially nonfibrillar at pH 7. The resulting nonfibrillar collagen is then mixed with a multifunctionally activated synthetic hydrophilic polymer in order to initiate crosslinking between the collagen and the synthetic polymer.

USE AND ADMINISTRATION

In a general method for effecting the attachment of a first surface to a second surface: 1) collagen and a multifunctionally activated synthetic hydrophilic polymer are provided; 2) the collagen and synthetic polymer are mixed together to initiate crosslinking between the collagen and the synthetic polymer; 3) the collagen—synthetic polymer mixture is applied to a first surface before substantial crosslinking has occurred between the collagen and the synthetic polymer; and 4) the first surface is contacted with a second surface to effect adhesion between the first surface and the second surface. At least one of the first and second surfaces is preferably a native tissue surface.

For example, the collagen and multifunctionally activated synthetic hydrophilic polymer are generally provided in separate syringes, the contents of which are then mixed together using a syringe-to-syringe mixing technique just prior to delivery to a first surface. As described above, the collagen may be nonfibrillar or fibrillar collagen, but is preferably nonfibrillar collagen. The nonfibrillar collagen may be a chemically modified collagen (such as methylated collagen); a collagen that is in nonfibrillar or microfibrillar form in its native state (such as type IV collagen); or fibrillar collagen that has been combined with a sufficient amount of a fiber disassembly agent to render the collagen substantially nonfibrillar at pH 7. The synthetic polymer is generally used in sterile, dry form (as described in commonly assigned, copending U.S. application Ser. No. 08/287,549, filed Aug. 8, 1994) to prevent the loss of crosslinking ability due to hydrolysis which typically occurs upon exposure of hydrophilic polymers to aqueous media.

The collagen and synthetic polymer are preferably mixed for a minimum of 20 (more preferably, at least 30) passes to ensure adequate mixing of the dry polymer with the collagen. As crosslinking between the collagen and the synthetic polymer is generally initiated during the mixing process, it is important to deliver the collagen—synthetic polymer reaction mixture to the first surface as soon as possible after mixing.

The collagen—synthetic polymer reaction mixture can be extruded onto the first surface from the opening of a syringe or other appropriate extrusion device. Following application, the extruded collagen—synthetic polymer reaction mixture can be spread over the first surface using a spatula, if necessary. Alternatively, the nonfibrillar collagen and synthetic polymer can be mixed together in an appropriate mixing dish or vessel, then applied to the first surface using a spatula.

Following application of the collagen—synthetic polymer reaction mixture, the first surface is contacted with a second surface. If the two surfaces are contacted before substantial crosslinking has occurred between the collagen and the synthetic polymer, synthetic polymer molecules will also covalently bond with lysine residues on collagen molecules present on either or both of the surfaces, providing improved adhesion.

The two surfaces may be held together manually or using other appropriate means while the crosslinking reaction is proceeding to completion. Crosslinking between the collagen and synthetic polymer is typically complete within 20 to 60 minutes after mixing of the collagen with the synthetic polymer.

At least one of the first and second surfaces is preferably a native tissue surface. As used herein, the term "native tissue" refers to biological tissues that are native to the body of the specific patient being treated, and that have not been displaced or removed from their original place of residence.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants), or biological tissues that have been removed from one pan of the body of a patient for implantation to another part of the body of the same patient (such as bone autografts, skin autografts, etc.). For example, the bioadhesive compositions of the present invention can be used to adhere a donor cornea to the eye of a recipient patient, or can be used to adhere a piece of skin from one part of a patient's body to another part of the body, as in the case of a burn victim.

As used herein, the term "synthetic implant" refers to any biocompatible material intended for implantation into the body of a patient not encompassed by the above definitions for native tissue and non-native tissue. Synthetic implants include, for example, synthetic blood vessels, heart valves, artificial organs, bone prostheses, implantable lenticules, etc.

Because of their optical clarity, nonfibrillar collagen-based bioadhesive compositions of the present invention are particularly well suited for use in ophthalmic applications. For example, a synthetic lenticule for correction of vision can be attached to the Bowman's layer of the cornea of a patient's eye using the methods of the present invention. As disclosed in commonly assigned, allowed U.S. application Ser. No. 08/147,227, filed Nov. 3, 1993, by Rhee et al., to which the present application claims priority, a chemically modified collagen (such as succinylated or methylated collagen) which is in substantially nonfibrillar form at pH 7 can be crosslinked using a synthetic hydrophilic polymer, then molded into a desired lenticular shape and allowed to complete crosslinking. The resulting crosslinked collagen lenticule can then be attached to the Bowman's layer of a de-epithelialized cornea of a patient's eye using the methods of the present invention. By applying the nonfibrillar collagen—synthetic polymer reaction mixture to the anterior surface of the cornea, then contacting the anterior surface of the cornea with the posterior surface of the lenticule before substantial crosslinking has occurred between the collagen and the synthetic polymer, the synthetic polymer will also covalently bind with collagen molecules in both the corneal tissue and the lenticule to firmly anchor the lenticule in place. (Alternatively, the reaction mixture can be applied first to the posterior surface of the lenticule, which is then contacted with the anterior surface of the cornea.)

Solutions of difunctionally activated SG-PEG (3800 MW) in PBS were prepared at different concentrations as follows: 10 mg SG-PEG in 0.1 ml PBS, 20 mg SG-PEG in 0.1 ml PBS, 50 mg SG-PEG in 0.1 ml PBS, and 100 mg SG-PEG in 0.2 ml PBS. Each of the four crosslinker solutions was mixed with 0.9 ml of the 20 mg/ml succinylated collagen using syringe-to-syringe mixing. The four succinylated collagen - SG-PEG compositions had final SG-PEG concentrations of 10, 20, 50, and 91 mg/ml, respectively. The final collagen concentration of the samples was approximately 18 mg/ml.

The four formulations were observed visually for signs of crosslinking at 5 minutes and 2 hours after mixing. As shown in Table 1, the succinylated collagen formulations containing 50 and 91 mg/ml SG-PEG showed signs of crosslinking 5 minutes after mixing. All four formulations showed significant crosslinking 2 hours after mixing, forming optically clear gels.

TABLE 1

| PEG Crosslinking of Succinylated Collagen | | | | | |
| --- | --- | --- | --- | --- | --- |
| SGPEG (mg) | PBS (ml) | Succinylated Collagen (ml) | Signs of Crosslinking? (5 minutes) | Signs of Crosslinking? (2 hours) | Final SGPEG Conc. (mg/ml) |
| 10 | 0.1 | 0.9 | no | yes | 10 |
| 20 | 0.1 | 0.9 | no | yes | 20 |
| 50 | 0.1 | 0.9 | some signs | yes | 50 |
| 100 | 0.2 | 0.9 | some signs | yes | 91 |

EXAMPLES

The following examples are put forth so as to provide those of ordinary skill in the an with a complete disclosure and description of how to make the preferred embodiments of the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

(Preparation of PEG Crosslinked Succinylated Collagen)

Six (6) liters of collagen-in-solution (CIS) (3 mg/ml collagen in pH 2 HCl) was adjusted to pH 9 using 0.1M NaOH at room temperature to produce fibrillar collagen. 1.35 grams of succinic anhydride powder was added to the fibrillar collagen and the pH maintained between 8.5 and 9, resulting in the formation of succinylated collagen. The pH of the succinylated collagen was adjusted to 7.2, then to 4.2 using 0.1M HCl to precipitate the succinylated collagen. The succinylated collagen was then centrifuged and the supernalant discarded. The pH of the pellet was adjusted to 7.2 using 0.1M NaOH. The succinylated collagen pellet was diluted in water and the collagen concentration of the resulting succinylated collagen solution determined to be 20 mg/ml.

The melting temperatures of the succinylated collagen formulations containing 10, 20, 50, and 91 mg/ml SG-PEG (Samples B, C, and D, respectively) were measured using differential scanning calorimetry (DSC) and compared with that of noncrosslinked succinylated collagen (Sample A). DSC is a measure of degree of crosslinking which is commonly used to evaluate gel stability.

DSC results are shown in FIG. 1. The melting temperatures for the crosslinked formulations (B, C, and D) were significantly higher than that for the noncrosslinked succinylated collagen (A).

Example 2

(Preparation of PEG Crosslinked Methylated Collagen)

Ninety (90) milliliters of Zyderm® II Collagen without lidocaine (Collagen Corporation, Palo Alto, Calif.), adjusted to 20 mg/ml collagen concentration, was lyophilized to form freeze-dried collagen. The freeze-dried collagen was then chopped into small pieces.

8.3 milliliters of concentrated hydrochloric acid and 30 grams of sodium sulfate were added to methanol to produce anhydrous acidic methanol. The sodium sulfate was then filtered off of the anhydrous acidic methanol. Approximately 1 liter of the acidified anhydrous methanol was subsequently mixed with the chopped freeze-dried collagen.

After incubation at room temperature for 7 days, methylated collagen was formed. The excess methanol was evaporated off. The resulting material was subsequently lyophilized and dialyzed and the collagen concentration was adjusted to 20 mg/ml by the addition of 0.02M $Na_2HPO_4$/ 0.13M NaCl, pH 7.3.

Solutions of difunctionally activated SG-PEG (3800 MW) in PBS were prepared at different concentrations as follows: 3 mg SG-PEG in 0.15 ml PBS, 9 mg SG-PEG in 0.15 ml PBS, 15 mg SG-PEG in 0.15 ml PBS, 30 mg SG-PEG in 0.15 ml PBS, 45 mg SG-PEG in 0.15 ml PBS, 75 mg SG-PEG in 0.15 ml PBS, 111 mg SG-PEG in 0.2 ml PBS, and 165 mg SG-PEG in 0.2 ml PBS. Each of the crosslinker solutions was mixed with 1.35 ml of the 20 mg/ml methylated collagen using syringe-to-syringe mixing. The methylated collagen—SG-PEG compositions had final SG-PEG concentrations of 2, 6, 10, 20, 30, 50, 72, and 106 mg/ml, respectively. The final collagen concentration of the samples was approximately 18 mg/ml.

The resulting formulations were evaluated qualitatively for elasticity and gel strength. As shown in Table 2, the formulations containing 30 and 50 mg/ml SG-PEG showed signs of crosslinking immediately upon mixing. The compositions containing 2, 6, 10, and 20 mg/ml SG-PEG required approximately 5 to 10 minutes for crosslinking. The compositions containing 72 and 106 mg/ml SG-PEG required longer than 10 minutes for gel formation, forming weak, inelastic gels. The compositions containing between 2–20 mg/ml SG-PEG resulted in the strongest, most elastic gels. The composition containing 30 mg/ml SG-PEG formed a gel with good strength, but low elasticity, which could be useful in applications where elasticity is not a desired characteristic. Compositions of methylated collagen containing greater than 30 mg/ml SG-PEG showed poor elasticity and gel strength. All gels were optically clear.

Figure 2:
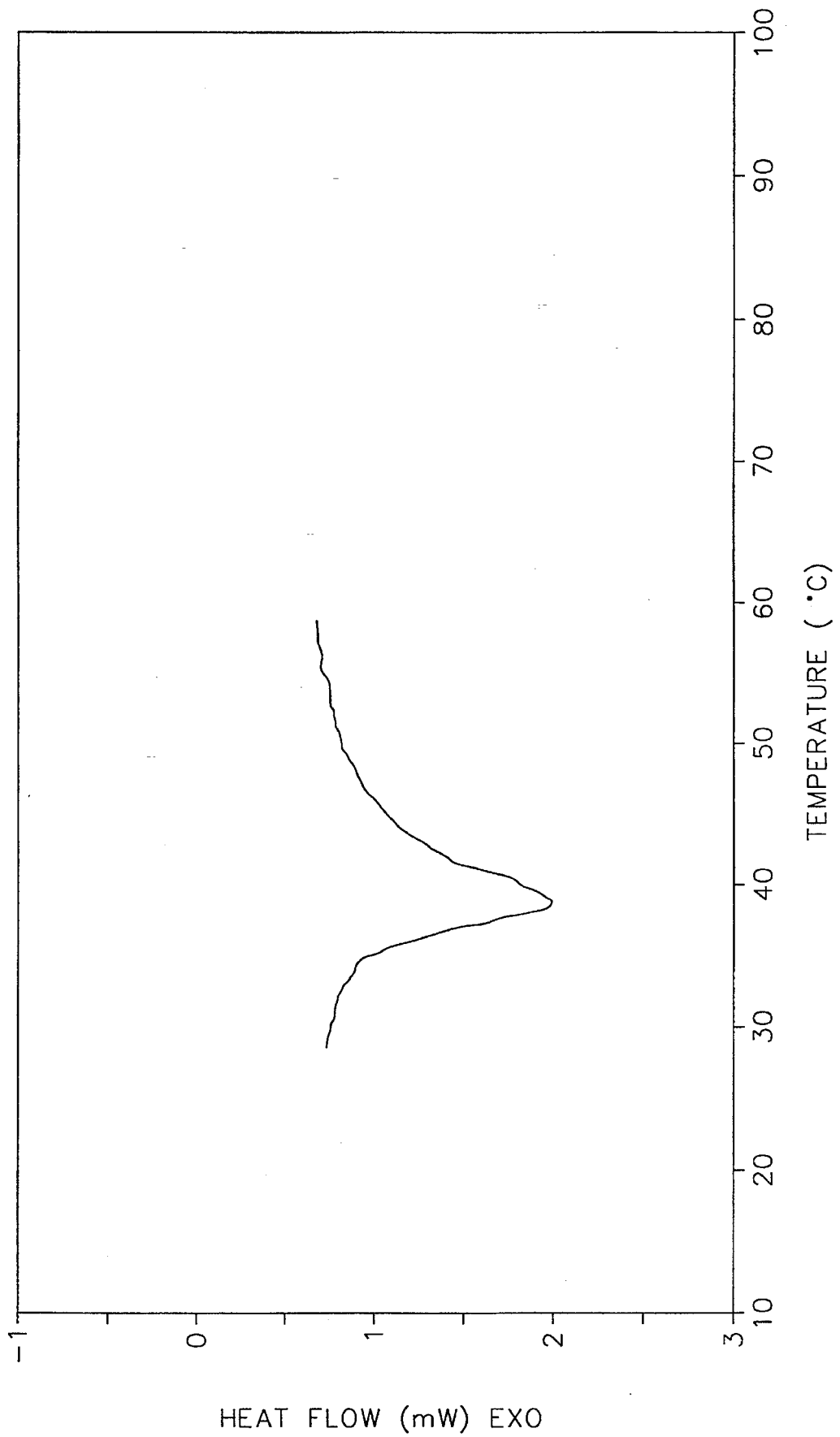
FIG. 2 shows DSC results for methylated collagen formulations containing 2, 10, 30, and 72 mg/ml difunctionally activated SG-PEG (Samples E, F, G, and H, respectively).
Figure 3:
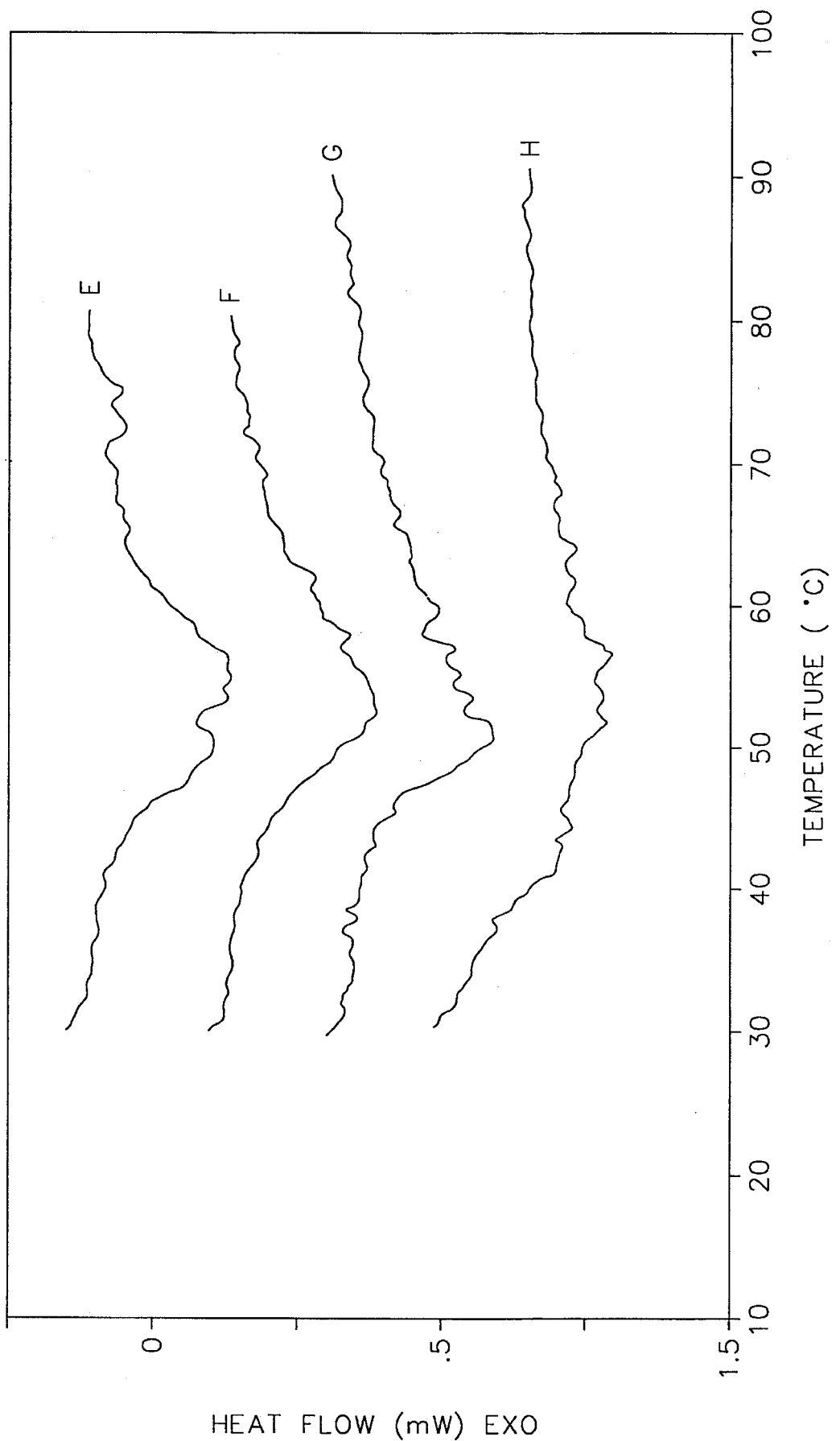
FIG. 3 shows DSC results for noncrosslinked methylated collagen.

The melting temperatures of the methylated collagen formulations containing 2, 10, 30, and 72 mg/ml SG-PEG (Samples E, F, G, and H respectively) were measured using differential scanning calorimetry (DSC) and compared with that of noncrosslinked methylated collagen. The DSC results for the noncrosslinked and crosslinked samples are shown in FIGS. 2 and 3, respectively. The melting curve profiles indicate that the crosslinked formulations contain a heterogeneous population of molecules, most of which melt at a higher temperature than the noncrosslinked collagen.

As shown in Table 2, the melting temperatures for the crosslinked formulations were significantly higher than that for the noncrosslinked methylated collagen.

removed using a blunt metal spatula. Following de-epithelialization, the cornea was washed with PBS and dried thoroughly using a sponge.

A solution of 10 mg difunctionally activated SG-PEG (3800 MW) in 0.1 ml PBS was prepared. The crosslinker solution was mixed with 0.9 ml of the 30 mg/ml methylated collagen using syringe-to-syringe mixing. Immediately following mixing, approximately 0.2 ml of the methylated collagen—SG-PEG material was extruded from the opening of the 1.0 cc syringe onto the surface of the de-epithelialized bovine cornea.

The methylated collagen—SG-PEG material was molded in place on the cornea using a polymethylmethacrylate (PMMA) or polysulfone mold. Crosslinking and gel formation of the collagen-polymer occurred within approximately three minutes to form a lenticule in situ on the bovine cornea.

Following gel formation, the mold was removed from the collagen-polymer material. The surface of the in situ formed lenticule was irrigated with PBS. The lenticule was secure and not dislodged by the irrigation. Gentle teasing of the lenticule with a spatula indicated that it was favorably attached to the cornea. The lenticule was able to be removed by "peeling" with a spatula.

Histological examination (at 100× magnification) was performed on the bovine cornea before and after removal of the methylated collagen—SG-PEG lenticule. Histological examination before lenticule removal indicated an intimate interface between the lenticule and the cornea. Following lenticule removal, the surface of the cornea showed no obvious damage or aberrations.

The above experiment was repeated using a material prepared from succinylated collagen, at a 36% level of succinylation and a 30 mg/ml collagen concentration. Twenty (20) milligrams of difunctionally activated SG-PEG was dissolved in 0.1 ml PBS. The crosslinker solution was subsequently mixed with 0.9 mg of the 30 mg/ml succinylated collagen using syringe-to-syringe mixing, then delivered to a de-epithelialized bovine cornea. Gel formation

TABLE 2

PEG Crosslinking of 20 mg/ml Methylated Collagen

| Final SG-PEG Conc. (mg/ml) | Time to Form Gel | Elasticity | Gel Strength | DSC Tm (°C.) Range |
| --- | --- | --- | --- | --- |
| 0 | — | — | — | 38–43 |
| 2 | 5–10 min. | elastic | good | 45–60 |
| 6 | 5–10 min. | elastic | good | — |
| 10 | 5–10 min. | very elastic | very good | 45–68 |
| 20 | 5 min. | slightly elastic | good | — |
| 30 | immediate | not elastic | good | 47–62 |
| 50 | immediate | slightly elastic | not good | — |
| 72 | >10 min. | not elastic | not good | 40–70 |
| 106 | >10 min. | not elastic | not good | — |

Example 3

(In vitro Delivery & Attachment of in situ Polymerizable Lenticule to Bovine Cornea)

Methylated collagen having a collagen concentration of 30 mg/ml was prepared as described in Example 2. The epithelial layer of the cornea of an excised bovine eye was occurred within approximately 10 minutes following delivery of the collagen-polymer material to the cornea. Qualitative comparison revealed the methylated collagen—SG-PEG material to have better attachment to the cornea than the succinylated collagen—SG-PEG material.

Example 4

(Use of PEG Crosslinked Methylated Collagen as a Bioadhesive)

The following formulations were prepared using methylated collagen (at various collagen concentrations) and various concentrations of difunctionally activated SG-PEG (3800 MW). The formulations were qualitatively assessed for adhesion to bloody wound sites in a previously sacrificed rabbit.

Formulation A:

Nine hundred (900) microliters (μl) of methylated collagen (prepared as described in Example 1), having a collagen concentration of 33 mg/ml, was mixed with approximately 13.5 mg of difunctionally activated SG-PEG (3800 MW) in 150 μl of PBS (phosphate-buffered saline) (40:1 molar ratio of SG-PEG to collagen). This material was extruded onto a bloody wound site on the liver of a previously sacrificed rabbit and allowed to gel for 1 minute. The skin was then placed on top of the gel and held in place for 1 minute. The skin was removed and the condition of the gel examined. The methylated collagen—SG-PEG gel adhered very well to the liver, not as well to the skin.

Formulation B:

Nine hundred (900) microliters (μl) of methylated collagen, having a collagen concentration of 33 mg/ml, was mixed with approximately 27 mg of difunctionally activated SG-PEG (3800 MW) in 150 μl of PBS (80:1 molar ratio of SG-PEG to collagen). This material was extruded onto a bloody wound site on the muscle of a previously sacrificed rabbit and allowed to gel for 1 minute. The skin was then placed on top of the gel and held in place for 1 minute. The skin was removed and the condition of the gel examined. The methylated collagen—SG-PEG gel adhered very well to the wound site, not as well to the skin.

Formulation C:

4.5 milliliters (ml) of methylated collagen, having a collagen concentration of 64 mg/ml, was mixed with approximately 325 mg of difunctionally activated SG-PEG (3800 MW) in 0.5 ml of PBS (100:1 molar ratio of SG-PEG to collagen). This material was extruded onto a bloody wound site of a previously sacrificed rabbit and allowed to gel for 1 minute. The skin was then placed on top of the gel and held in place for 1 minute. The skin was removed and the condition of the gel examined. The methylated collagen—SG-PEG gel adhered very well to the wound site, not as well to the skin.

Formulation D:

1.8 milliliters (ml) of methylated collagen, having a collagen concentration of 35 mg/ml, was mixed with 71.4 mg of difunctionally activated SG-PEG (3800 MW) in 250 μl of PBS (100:1 molar ratio of SG-PEG to collagen). The material was mixed using syringe-to-syringe mixing for 30 passes of material between syringes, then extruded onto a bloody wound site of a previously sacrificed rabbit. A collagen—SG-PEG membrane (approximate diameter: 4.5 cm) containing a 2:1 molar ratio of SG-PEG to collagen was immediately placed on top of the extruded SG-PEG—collagen material, which was allowed to gel for 1 minute. The skin was then placed on top of the membrane and held in place for 1 minute. The skin was removed and the condition of the gel and the membrane examined. The methylated collagen—SG-PEG gel adhered very well to the wound site and to the membrane.

Formulation E:

1.8 milliliters (ml) of methylated collagen, having a collagen concentration of 35 mg/ml, was mixed with 71.4 mg of difunctionally activated SG-PEG (3800 MW) in 250 μl of PBS (100:1 molar ratio of SG-PEG to collagen). The material was mixed using syringe-to-syringe mixing for 30 passes of material between syringes, then extruded onto a bloody wound site of a previously sacrificed rabbit, then allowed to gel for 1 minute. The skin was then placed on top of the gel and held in place for 1 minute. The skin was removed and the condition of the gel examined. The methylated collagen—SG-PEG gel adhered very well to the wound site, not as well to the skin.

Example 5

(Bioadhesive Formulations Comprising Mixtures of Methylated Collagen and Fibrillar Collagen Crosslinked With PEG)

The following experiments were performed to assess the adhesion of PEG-crosslinked fibrillar collagen to bovine eyes (obtained from Ferara Meats, Santa Clara, Calif.). The experiments were perforated less than 24 hours following harvest of the eyes from the sacrificed animals. The eyes were washed and soaked in PBS.

Three eyes were de-epithelialized, washed in PBS, then dried. Three formulations were evaluated, as follows:

Fibrillar collagen (68 mg/ml collagen concentration) was mixed with difunctionally activated SG-PEG (3800 MW) in a 20:1 molar ratio of SG-PEG to collagen, then immediately applied to a de-epithelialized eye.

Fibrillax collagen (68 mg/ml collagen concentration) was mixed with difunctionally activated SG-PEG in a 20:1 molar ratio of SG-PEG to collagen, the formulation was centrifuged to remove air bubbles, then applied to a de-epithelialized eye approximately 2 minutes after mixing.

Methylated collagen (37.2 mg/ml collagen concentration) was mixed with difunctionally activated SG-PEG in a 20:1 molar ratio of SG-PEG to collagen, then immediately applied to a de-epithelialized eye. Fibrillax collagen (68 mg/ml collagen concentration) was mixed with difunctionally activated SG-PEG in a 20:1 molar ratio of SG-PEG to collagen, then immediately applied on top of the methylated collagen—SG-PEG formulation.

After 2 hours at room temperature, attachment of the collagen—SG-PEG formulations to the eyes was qualitatively assessed. The compositions comprising fibrillax collagen and SG-PEG were found to have no attachment to the de-epithelialized eyes. The composition comprising methylated collagen and SG-PEG was found to adhere very well to the deepithelialized eye.

The formulations set forth in Table 3, below, were prepared by mixing fibrillax collagen (37.2 mg/ml collagen concentration) with methylated collagen (37.2 mg/ml collagen concentration), then crosslinking using 0.4% (weight/volume) difunctionally activated SG-PEG (3800 MW).

TABLE 3

Bioadhesive Formulations Comprising Mixtures of Methylated Collagen and Fibrillar Collagen Crosslinked Using Difunctionally Activated SG-PEG

| Fibrillar Collagen (g) | Methylated Collagen (g) | % (w/w) Fibrillar Collagen |
|---|---|---|
| 0.72 | 0.18 | 80 |
| 0.63 | 0.27 | 70 |
| 0.54 | 0.36 | 60 |
| 0.45 | 0.45 | 50 |

TABLE 3-continued

Bioadhesive Formulations Comprising Mixtures of Methylated Collagen and Fibrillar Collagen Crosslinked Using Difunctionally Activated SG-PEG

| Fibrillar Collagen (g) | Methylated Collagen (g) | % (w/w) Fibrillar Collagen |
|---|---|---|
| 0.36 | 0.54 | 40 |
| 0.27 | 0.63 | 30 |

Each of the six formulations was applied to a de-epithelialized bovine eye. The formulations all adhered well to the de-epithelialized eyes; however, strength of attachment was found to increase with increasing methylated collagen content (i.e., decreasing fibrillax collagen content) of the formulation.

Example 6

(In vivo Adhesion of Various Collagen-based Formulations)

The bladder of a previously sacrificed pig was cut open and 0.2 cc each of various collagen-based formulations, as set forth in Table 4, below, were injected from a 1-cc syringe through a 27-gauge needle into the inner bladder wall. The pig bladder was then covered with a damp towel (to keep the tissue moist) and incubated at 37° C. for approximately one (1) hour.

The tissue covering the upper surface of the implants was excised to reveal the implants. The attachment of each of the implants to the underlying tissue was assessed qualitatively, as set forth in Table 4, below.

TABLE 4

Attachment of Various Collagen-based Formulations to Pig Bladder Wall

| Material | Gel Formation | Attachment to Tissue |
|---|---|---|
| Zyplast ® I Collagen (glutaraldehyde crosslinked fibrillar collagen, 35 mg/ml collagen concentration) | None | None |
| Zyplast II Collagen (glutaraldehyde crosslinked fibrillar collagen, 65 mg/ml collagen concentration) | None | None |
| Zyderm ® I Collagen (noncrosslinked fibrillar collagen, 35 mg/ml collagen concentration) | Firm gel | Strong |
| 70:30 (w/w) mixture of Zyplast I & Zyderm I Collagens, crosslinked with 0.3% (w/v) DSE-PEG* | Firm gel | Strong |
| Methylated collagen (noncrosslinked nonfibrillar collagen, 35 mg/ml collagen concentration) crosslinked with 0.3% (w/v) DSE-PEG* | Soft gel | Weak |

*DSE-PEG = Difunctionally activated SE-PEG, 3800 MW

All of the PEG-crosslinked formulations showed attachment to tissue, although the PEG-crosslinked compositions comprising fibrillar collagen showed stronger attachment than did the PEG-crosslinked nonfibrillar (methylated) collagen formulation, indicating that the ratios of DSE-PEG to methylated collagen used in this experiment were not optimal.

Example 7

(Preparation of Collagen-based Bioadhesive Compositions)

One (1) milliliter of glycerol (obtained from Sigma St. Louis, Mo.) was autoclaved for sterilization. A 3-cc syringe containing 1 ml of Zyderm® II Collagen (65 mg/ml collagen protein concentration, obtained from Collagen Corporation, Palo Alto, Calif.) was attached to the syringe containing glycerol via a three-way stopcock. The glycerol and collagen were then mixed for approximately 100 passes using syringe-to-syringe mixing.

One (1) gram of sucrose (obtained from Sigma, St. Louis, Mo.) was weighed into a weigh boat. One milliliter of Zyderm II Collagen was added to the sucrose in the weigh boat. The sucrose and collagen were mixed until the collagen became clear. The collagen—sucrose mixture was filled into a 3-cc syringe.

The glycerol—collagen and sucrose—collagen mixtures were then mixed with various quantities of sterile, dry, difunctionally activated SG-PEG (DSG-PEG, 3800 MW), contained within a 3-cc syringe, using syringe-to-syringe mixing. When the collagen formulation and DSG-PEG had been adequately mixed, the resulting composition could be extruded onto a surface, then contacted with a second surface, to effect adhesion between the two surfaces.

Example 8

(Characterization of Collagen-based Bioadhesive Compositions)

The formulations listed in Table 5 were prepared, according to the methods described in the Examples above, and evaluated qualitatively for adhesion characteristics (i.e., tackiness) and form (i.e., handling properties). The formulations were rated on a scale of 0 to 3, with a rating of 3 indicating that the formulation was very tacky or had very good form, and a rating of 0 indicating that the formulation had poor tackiness or form.

TABLE 5

| | | | | Characterization of Collagen-based Bioadhesive Formulations | | |
|---|---|---|---|---|---|---|
| Formulation | Temp. (°C.) | pH | Collagen Conc. (mg/ml) | DSG-PEG Conc. (% wt) | Adhesion | Form |
| DC/DSG-PEG | >40 | 7 | 100–150 | 1 | 2 | 2 |
| DC/DSG-PEG | >40 | 7 | 100–150 | 0.1 | 2 | 2 |
| MC/DSG-PEG | 20 | 7 | 60 | 1 | 1 | 1 |
| MC/DSG-PEG | 20 | 7 | 60 | 0.1 | 2 | 2 |
| MC/DSG-PEG | >40 | 7 | 60 | 1 | 1 | 1 |
| MC/DSG-PEG | >40 | 7 | 60 | 0.1 | 2 | 3 |
| SC/DSG-PEG | 20 | 7 | 50 | 1 | 3 | 3 |
| GC/DSG-PEG | 20 | 7 | 65 | 1 | 3 | 3 |
| GC/DSG-PEG | 20 | 7 | 65 | 0.1 | 3 | 3 |
| GC/DSG-PEG | 20 | 7 | 35 | 1 | 3 | 3 |
| GC/DSG-PEG | 20 | 7 | 35 | 0.1 | 3 | 3 |

DC = Denatured collagen (ie., gelatin)
MC = Methylated collagen
SC = Sucrose/collagen
GC = Glycerol/collagen All of the sucrose/collagen/DSG-PEG and glycerol/collagen/DSG-PEG formulations demonstrated excellent adhesion characteristics and handling properties. The methylated collagen/DSG-PEG formulations did not show quite as good adhesion and handling characteristics, indicating that the ratios of DSG-PEG to methylated collagen used in this experiment were not optimal.

The present invention is shown and described herein at what is considered to be the most practical, and preferred embodiments. It is recognized, however, that departures may be made therefrom which are within the scope of the invention and that obvious modifications will occur to one skilled in the art upon reading this disclosure.

What is claimed is:

1. A composition comprising fibrillar collagen, a fiber disassembly agent, and a multifunctionally activated synthetic hydrophilic polymer, wherein the fiber disassembly agent is present in an amount sufficient to render the collagen substantially nonfibrillar at pH 7, wherein the collagen and synthetic polymer covalently bind to form a collagen—synthetic polymer conjugate, and wherein the fiber disassembly agent is selected from the group consisting of: a biocompatible alcohol, an amino acid, an inorganic salt, and a carbohydrate.

2. The composition of claim 1, wherein the fiber disassembly agent is a biocompatible alcohol selected from the group consisting of glycerol and propylene glycol.

3. The composition of claim 1, wherein the multifunctionally activated synthetic hydrophilic polymer is a multifunctionally activated polyethylene glycol.

4. The composition of claim 3, wherein the multifunctionally activated polyethylene glycol is selected from the group consisting of difunctionally activated SG-PEG and difunctionally activated SE-PEG.

5. A composition comprising fibrillar collagen, a biocompatible alcohol, and a multifunctionally activated synthetic hydrophilic polymer, wherein the biocompatible alcohol is present in an amount sufficient to render the collagen substantially nonfibrillar at pH 7, and wherein the collagen and synthetic polymer covalently bind to form a collagen—synthetic polymer conjugate.

6. The composition of claim 5, wherein the fiber disassembly agent is a biocompatible alcohol selected from the group consisting of glycerol and propylene glycol.

7. The composition of claim 5, wherein the multifunctionally activated synthetic hydrophilic polymer is a multifunctionally activated polyethylene glycol.

8. The composition of claim 1, wherein the multifunctionally activated polyethylene glycol is selected from the group consisting of difunctionally activated SG-PEG and difunctionally activated SE-PEG.

\* \* \* \* \*